United States Patent [19]

Itoh et al.

[11] Patent Number: 4,654,328
[45] Date of Patent: Mar. 31, 1987

[54] METHOD FOR CONTROLLING SANITARY AND AGRICULTURAL PESTS

[75] Inventors: Koichi Itoh; Yoshiaki Nishimura, both of Tokyo, Japan

[73] Assignee: Shin-Etsu Chemical Co., Ltd., Tokyo, Japan

[21] Appl. No.: 670,744

[22] Filed: Nov. 13, 1984

[51] Int. Cl.$^4$ ............................................. A01N 55/00
[52] U.S. Cl. ........................................................ 514/63
[58] Field of Search ............................ 424/184; 514/63

[56] References Cited

U.S. PATENT DOCUMENTS 3,652,628 3/1972 Hyde et al. ........................... 424/184
4,146,619 3/1979 Lover et al. .......................... 424/184

OTHER PUBLICATIONS

Derwent, 092, Japan, 84-092336115, (published 3–5-84).
Chemical Abstracts, 92: 192752r, (10, Jan. 1980).
Chemical Abstracts, 90: 67756c (14, Dec. 1978).
Chemical Abstracts, 66: 75273n (20, Nov. 1966).

Primary Examiner—Albert T. Meyers
Assistant Examiner—John M. Kilcoyne
Attorney, Agent, or Firm—Toren, McGeady & Goldberg

[57] ABSTRACT

The invention provides a novel method for controlling various kinds of pests harmful against sanitation and agriculture by applying an organosilicon compound, never used hitherto for such a purpose, to the body of the pest or distributing the organosilicon compound over the site or field infested therewith. The organosilicon compound is a cyclic organopolysiloxane compound represented by the general formula

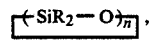

in which each of the groups R is a hydrogen atom or a monovalent hydrocarbon group independently from the others, at least one of the groups denoted by R in a molecule being a monovalent hydrocarbon group, and n is an integer in the range from 3 to 7.

2 Claims, No Drawings

METHOD FOR CONTROLLING SANITARY AND AGRICULTURAL PESTS

BACKGROUND OF THE INVENTION

The present invention relates to a novel method for controlling sanitary and agricultural pests or, more particularly, to a method for controlling sanitary and agricultural pests using a relatively inexpensive compound having absolutely no toxic effect to mammals including man and useful or domestic animals and not used hitherto as an insecticide.

Needless to say, a great number of synthetic and naturally occurring compounds have been proposed and practically used as an insecticide to control the population of various pests, i.e. noxious insects, harmful against sanitation of human life and agricultural art including forestry, horticulture and the like. Most of the prior art insecticidal compounds are expensive which limits the applicability of the compound from the economic standpoint. Moreover, in recent years, certain species of insects exposed to a particular insecticide compound rapidly acquire strong resistance against the compound so that the insecticidal effect initially expected to the compound is lost within a relatively short period of time after the insecticide compound has come into practical application.

Even worse, most of the hitherto known insecticide compounds or especially those prepared synthetically are not free from the problem of toxicity to the human body and domestic animals and accumulation of insecticide compounds in environment is one of the problems of very serious public concern from the standpoint of environment reservation.

Thus, it is eagerly desired to develop a method for controlling ectoparasitic or non-ectoparasitic pests on human and animal bodies or household sites as well as agricultural pests in the field without the problems of high cost, acquired resistance and toxicity of the insecticide compound.

Recently, a pediculicidal method has been disclosed in U.S. Pat. No. 4,146,619 according to which application of a linear organosiloxane polymer having repeating units $R_2SiO$ in which each R is an alkyl or aryl group and having a viscosity of less than about 20,000 centistokes to an animal or human in need of controlling lice is effective for the purpose. This method is, however, not quite powerful for controlling ectoparasites and their ova and, moreover, less effective to the pests other than lice.

SUMMARY OF THE INVENTION

It is therefore an object of the present invention to provide a novel method for controlling pests which are harmful to humans and animals and agricultural pests in the fields while avoiding the problems of cost, acquired resistance and toxicity of the insecticide compound to mammals.

Thus, the method of the present invention for controlling harmful pests against sanitation and agriculture comprises applying a cyclic organopolysiloxane compound represented by the general formula

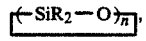 (1)

in which each R is a hydrogen atom or a monovalent hydrocarbon group independently from the others, at least one of the groups denoted by R in a molecule being a monovalent hydrocarbon group, and n is an integer in the range from 3 to 7, to the body of the pest or distributing the organopolysiloxane compound over the site or field infested with the pests.

DETAILED DESCRIPTION OF THE PREFERRED EMBODIMENTS

As is understood from the above described summary of the invention, the scope of the invention consists in the use of a specific organosilicon compound, which has never been used hitherto as an insecticide, for the purpose of insecticide against the pests. Namely, the inventors have discovered, as a result of their extensive investigations, that the above specified organosilicon compound can exhibit a very powerful and immediate insecticidal effect against various pests harmful in sanitation and agriculture and the use of the compound as the insecticide can overcome the problems unavoidable in the prior art insecticide compounds.

The cyclic organopolysiloxane compound used as the insecticide in the inventive method is represented by the general formula (1) given above, in which each of the groups denoted by R in a molecule is independent from the others, a hydrogen atom or a monovalent hydrocarbon group exemplified by alkyl groups such as methyl, ethyl and propyl groups, cycloalkyl groups such as cyclopentyl and cyclohexyl groups, alkenyl groups such as vinyl and allyl groups, aryl groups such as phenyl and tolyl groups and aralkyl groups such as benzyl and phenylethyl groups as well as those substituted groups obtained by the replacement of a part or all of the hydrogen atoms in the above named hydrocarbon groups with substituent atoms or groups such as halogen atoms and cyano groups. The groups denoted by R in a molecule may be of the same kind or different kinds although at least one of the groups denoted by R in a molecule should be a monovalent hydrocarbon group. The suffix n in the formula (1) is an integer in the range from 3 to 7.

The above defined organosilicon compounds can readily be prepared according to the known procedures described in many patent literatures and textbooks including, for example, Chemistry and Technology of Silicones by Walter Noll, 1968, Academic Press, New York and London.

The type of the cyclic organopolysiloxane compound used in the inventive method is not particularly limitative provided that the compound is liquid at room temperature and stable over a substantial length of time. Preferably, the compound should have a boiling point of 150° C. or higher under normal pressure and a viscosity of less than about 1000 centistokes at 25° C.

Several of the particular examples of the cyclic organopolysiloxane compounds suitable for use in the inventive method are as follows denoting methyl, ethyl, propyl, vinyl and phenyl groups with the symbols of Me, Et, Pr, Vi and Ph, respectively:

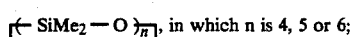, in which n is 4, 5 or 6; (I)

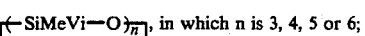, in which n is 3, 4, 5 or 6; (II)

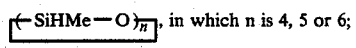, in which n is 4, 5 or 6; (III)

-continued

 (IV)

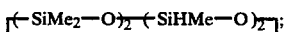, in which n is 3 or 4; (V)

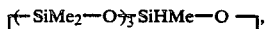; (VI)

. (VII)

, in which n is 3 or 4; (VIII)

, in which n is 3 or 4; (IX)

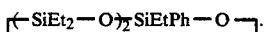; and (X)

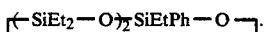. (XI)

It is of course optional that two kinds or more of the above named cyclic organopolysiloxanes are used in combination according to need.

The method of the present invention is performed by applying the above described cyclic organopolysiloxane compound to the body of the pest or distributing the compound over the site or field infested with the pests as a pesticide. It is of course possible that the cyclic organopolysiloxane compound is used as such but it is a preferable way that the cyclic organopolysiloxane compound as the effective constituent is admixed, according to known procedures and formulations, with various kinds of additives including carriers, extenders, diluents, spreading agents, propellants and the like according to need to form a pesticide composition which may be, for example, in an oily, emulsion-like, powdery, creamy or gel-like form or in the form of an aerosol-type spray suitable for the particular application intended. The method and instrument for applying or distributing the pesticide composition naturally depend on the form of the composition and as well as the kind of the pests and the condition of the site or field where the pesticide composition is distributed.

The cyclic organopolysiloxane compounds used as an insecticide in the inventive method are effective to almost all kinds of noxious insects and arachnids including flies, mosquitos, cockroaches, fleas, lice, mites, ticks and the like ectoparasitic and non-extoparasitic pests harmful to good sanitation and leaf hoppers, cutworms, diamond-back moths, leaf folders, aphids, rice borers and the like pests in agriculture. Further, the insecticidal effectiveness of the cyclic organopolysiloxane compounds is not limited to a specific stage in the whole life cycle of the pests but the compounds are effective throughout the whole stages of the life cycle of the pests including ova or nits, larvae, chrysalises and imagoes.

Following are the examples to illustrate the insecticidal effectiveness of the cyclic organopolysiloxane compounds used in the inventive method but not to limit the scope of the invention in any way. In the following examples, the cyclic organopolysiloxane compounds denoted by (I-1), (I-2) and (I-3) are the compounds of the above given formula (I) of which the suffix n is 4, 5 or 6, respectively, the compounds denoted by (II-1) and (II-2) are the compounds of the formula (II) of which the suffix n is 3 or 4, respectively, the compounds denoted by (III-1) and (III-2) are the compounds of the formula (III) of which the suffix n is 4 or 5, respectively, and the compound denoted by (V-1) is the compound of the formula (V) of which the suffix n is 3.

EXAMPLE 1

Sheets of filter paper were each coated with one of the cyclic organopolysiloxane compounds indicated in Table 1 below in a coating amount of 50 ml/m² and each 20 individuals of first age larvae of housefly and first age larvae of Croton bug were released on the thus treated filter paper to freely crawl thereon for 1 hour. The numbers of the survived individuals were counted after 24 hours to give the results shown in Table 1 by the percentages of the killed larvae.

TABLE 1

| Cyclic organo-polysiloxane | Housefly larvae killed, % | Croton bug larvae killed, % |
|---|---|---|
| (I-1) | 80 | 85 |
| (I-2) | 100 | 100 |
| (I-3) | 100 | 100 |
| (III-1) | 80 | 80 |
| (III-2) | 95 | 90 |
| (II-1) | 100 | 100 |
| (II-2) | 100 | 100 |
| (IV) | 100 | 100 |
| (V-1) | 90 | 95 |
| (X) | 90 | 90 |
| (XI) | 90 | 90 |

EXAMPLE 2

Each 15 nits of common gnat, housefly, acarid, and Croton bug were dipped in one of the cyclic organopolysiloxanes indicated in Table 2 below for 2 minutes and taken out thereof followed by removal of the organopolysiloxane adhering thereto with a paper towel. The thus treated nits were kept and incubated in a thermostated room at 25° C. for their respective nit stages and the numbers of the unhatched nits were counted to give the results shown in Table 2 in % of the unhatched nits.

TABLE 2

| Cyclic or-organopoly-siloxane | Unhatched nits, % | | | |
|---|---|---|---|---|
| | Common gnat | Housefly | Acarid | Croton bug |
| (I-1) | 75 | 75 | 80 | 75 |
| (I-2) | 95 | 95 | 95 | 95 |
| (I-3) | 100 | 100 | 100 | 100 |
| (III-1) | 70 | 70 | 75 | 70 |
| (III-2) | 90 | 90 | 90 | 90 |
| (II-1) | 100 | 100 | 100 | 100 |
| (II-2) | 100 | 100 | 100 | 100 |
| (IV) | 100 | 100 | 100 | 100 |
| (V-1) | 100 | 100 | 100 | 100 |
| (X) | 100 | 100 | 100 | 95 |

EXAMPLE 3

15 Individual specimens of final age larvae of housefly, first age larvae of Croton bug and imagoes of acarid were dipped in one of the cyclic organopolysiloxane compounds indicated in Table 3 below and immediately taken out thereof followed by removal of the organopolysiloxane compound adhering to the body by wiping with a paper towel. The thus treated larvae and imagoes were kept at 30° C. and the numbers of the killed individuals were counted after 1 hour to give the results shown in Table 3 below by the percentages of the killed individuals.

TABLE 3

| Cyclic organopolysiloxane | Housefly larvae killed, % | Croton bug larvae killed, % | Acarid imagoes killed % |
|---|---|---|---|
| (I-1) | 80 | 80 | 80 |
| (I-2) | 90 | 90 | 95 |
| (I-3) | 100 | 100 | 100 |
| (III-1) | 75 | 75 | 70 |
| (III-2) | 90 | 85 | 90 |
| (II-1) | 100 | 100 | 100 |
| (II-2) | 100 | 100 | 100 |
| (IV) | 100 | 100 | 100 |
| (V-1) | 100 | 100 | 100 |
| (X) | 100 | 100 | 100 |

EXAMPLE 4

A mixture composed of 90% and 10% by weight of the cyclic organopolysiloxanes (I-1) and (I-2) (see Example 1), respectively, was sprayed onto a rose tree having a swarm of rose aphids. A few minutes after spraying, all of the pests were dead.

What is claimed is:

1. A method for controlling insects which comprises applying an insecticidally effective amount of a cyclic organopolysiloxane compound which is liquid at room temperature having the formula

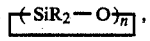

in which
R may be the same or different and is a hydrogen atom, or a monovalent hydrocarbon group selected from the group consisting of alkyl, cycloalkyl, alkenyl, aryl, aralkyl and halogen substituted aralkyl, wherein at least one of the groups denoted by R is a monovalent hydrocarbon group, and
n is an integer from 3 to 7,
directly to the pests or to a site infested with the pests.

2. The method of claim 1 wherein the organopolysiloxane compound is selected from the group consisting of

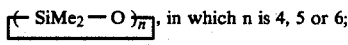, in which n is 4, 5 or 6;                           (I)

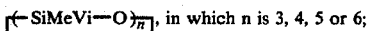, in which n is 3, 4, 5 or 6;                        (II)

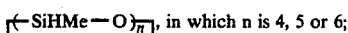, in which n is 4, 5 or 6;                           (III)

;                                                       (IV)

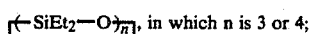, in which n is 3 or 4;                              (V)

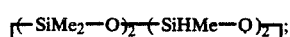;                                                       (VI)

,                                                      (VII)

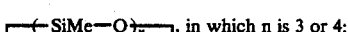, in which n is 3 or 4;                              (VIII)

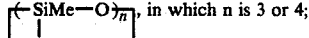, in which n is 3 or 4;                             (IX)

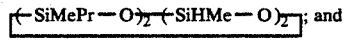; and                                                (X)

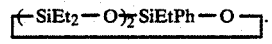.                                                     (XI)

* * * * *